(12) United States Patent
Beale et al.

(10) Patent No.: US 10,335,231 B2
(45) Date of Patent: Jul. 2, 2019

(54) MICROWAVE APPLICATOR AND METHOD OF FORMING A MICROWAVE APPLICATOR

(71) Applicant: Emblation Limited, Alloa (GB)

(72) Inventors: Gary Beale, Alloa (GB); Eamon McErlean, Alloa (GB)

(73) Assignee: EMBLATION LIMITED, Alloa (GB)

( * ) Notice: Subject to any disclaimer, the term of this patent is extended or adjusted under 35 U.S.C. 154(b) by 140 days.

(21) Appl. No.: 14/364,404

(22) PCT Filed: Dec. 14, 2012

(86) PCT No.: PCT/GB2012/053146
§ 371 (c)(1),
(2) Date: Jun. 11, 2014

(87) PCT Pub. No.: WO2013/088169
PCT Pub. Date: Jun. 20, 2013

(65) Prior Publication Data
US 2015/0045785 A1 Feb. 12, 2015

(30) Foreign Application Priority Data
Dec. 14, 2011 (GB) .................................. 1121436.8

(51) Int. Cl.
A61B 18/18 (2006.01)
H05B 6/70 (2006.01)
H05B 6/72 (2006.01)
B05D 5/00 (2006.01)
B29C 45/00 (2006.01)
B29L 31/34 (2006.01)

(52) U.S. Cl.
CPC ............ *A61B 18/1815* (2013.01); *B05D 5/00* (2013.01); *B29C 45/0001* (2013.01); *H05B 6/70* (2013.01); *H05B 6/701* (2013.01); *H05B 6/72* (2013.01); *B29L 2031/34* (2013.01)

(58) Field of Classification Search
CPC .................................................. A61B 18/1815
See application file for complete search history.

(56) References Cited

U.S. PATENT DOCUMENTS

| 3,087,129 A | 4/1963 | Maury et al. |
| 3,123,467 A | 4/1964 | Noschese |
| 3,128,467 A | 4/1964 | Lanctot |
| 3,421,115 A | 1/1969 | Staats |
| 3,448,384 A | 6/1969 | Scott |
| 3,942,138 A | 3/1976 | Schaedla |

(Continued)

FOREIGN PATENT DOCUMENTS

| FR | 2928848 | 9/2009 |
| WO | 9841800 | 9/1998 |
| WO | 03034790 | 4/2003 |

OTHER PUBLICATIONS

International Search Report and Written Opinion for PCT/GB2012/053146 dated Apr. 19, 2013.

*Primary Examiner* — Luther Behringer
(74) *Attorney, Agent, or Firm* — Snell & Wilmer, L.L.P.

(57) ABSTRACT

A method of forming a microwave applicator comprising forming a body comprising dielectric material so that there is a void in the dielectric material, and depositing conductive material in the void to form a feed for coupling energy into the dielectric material.

27 Claims, 12 Drawing Sheets

(56) References Cited

U.S. PATENT DOCUMENTS

| | | | |
|---|---|---|---|
| 4,392,039 A | 7/1983 | Risman | |
| 6,277,113 B1* | 8/2001 | Berube | A61B 18/1492 |
| | | | 606/33 |
| 6,287,302 B1* | 9/2001 | Berube | A61B 18/1815 |
| | | | 606/33 |
| 6,323,818 B1* | 11/2001 | Koh | H01Q 1/38 |
| | | | 343/772 |
| 6,822,542 B2 | 11/2004 | Clark et al. | |
| 6,823,218 B2* | 11/2004 | Berube | A61B 18/1492 |
| | | | 606/33 |
| 7,922,529 B1 | 4/2011 | Meurer | |
| 8,906,007 B2* | 12/2014 | Bonn | A61B 18/1815 |
| | | | 606/33 |
| 9,033,971 B2* | 5/2015 | Hancock | A61B 18/18 |
| | | | 606/33 |
| 2003/0106891 A1 | 6/2003 | Fagrell et al. | |
| 2008/0145518 A1* | 6/2008 | Maeda | H01L 21/4857 |
| | | | 427/58 |
| 2008/0314894 A1 | 12/2008 | Cronin | |
| 2011/0040300 A1* | 2/2011 | Brannan | A61B 18/18 |
| | | | 606/41 |

\* cited by examiner

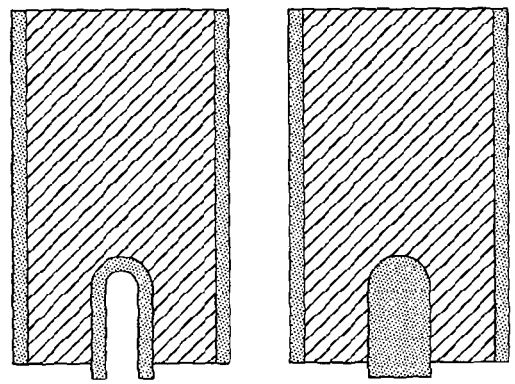
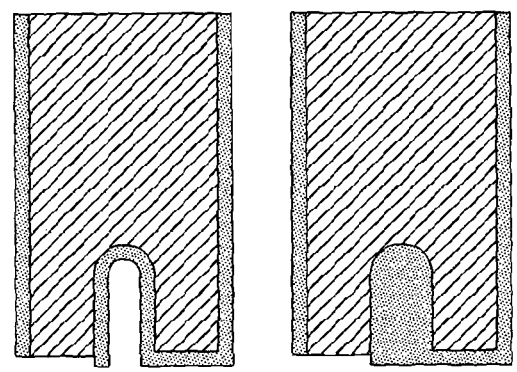
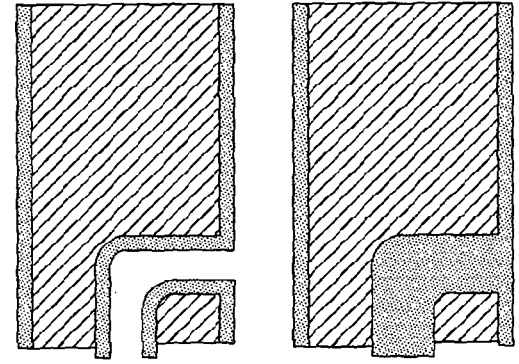
Fig. 2

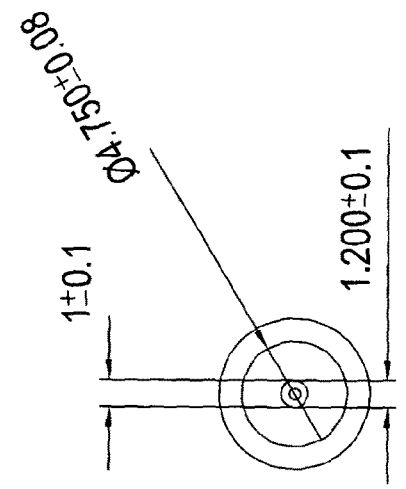
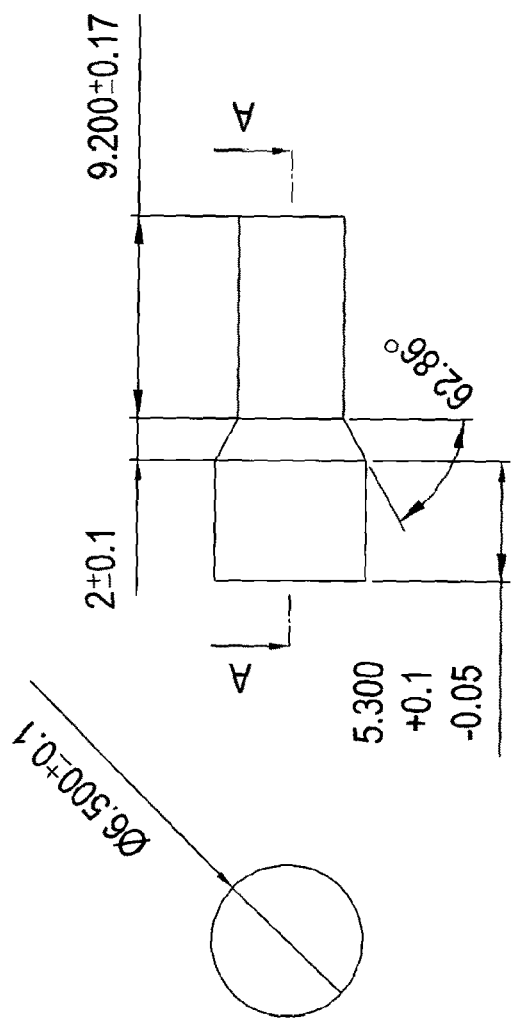
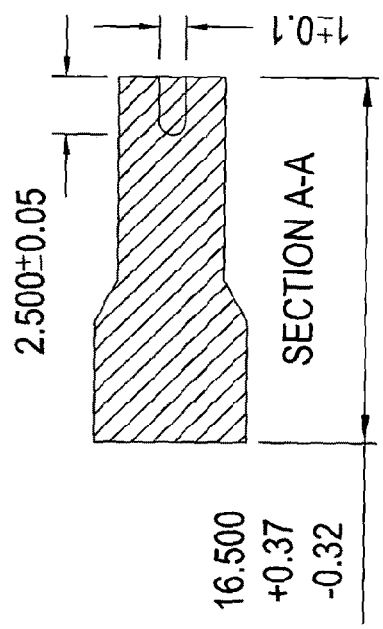
Fig. 11

MICROWAVE APPLICATOR AND METHOD OF FORMING A MICROWAVE APPLICATOR

CROSS-REFERENCE TO RELATED APPLICATIONS

This application is a U.S. national phase filing under 35 U.S.C. § 371 of PCT/GB2012/053146 filed Dec. 14, 2012 and claims priority from GB Applications No. 1121436.8 which was filed on Dec. 14, 2011, all of which are incorporated herein by reference in their entirety.

FIELD OF THE INVENTION

This invention relates to a microwave applicator, a coupling for a microwave applicator and to methods of fabricating a microwave applicator. The microwave applicator may comprise a disposable applicator suitable for radiating microwave energy into a target for the purposes of heating, such as surface tissue, for example skin or organ surfaces or any other material. The applicator of the invention may be used in medical microwave applications to treat or remove unwanted tissues or conditions affecting tissues.

BACKGROUND TO THE INVENTION

Microwave applicators employed to deliver energy in microwave heating applications are widely known. Often radiating elements are used to couple the energy into the target to be heated. These radiating elements are either probe-like antennas which are placed inside the heating target or waveguide structures that contain the energy within their internal dielectric that interfaces with a surface of the target to pass on the energy.

A number of these surface applicators exist, for example U.S. Pat. No. 4,392,039 describes a dielectric heating applicator having a cylindrical metal body filled with a mass of low loss dielectric material to be used in direct contact with a body to form a resonant element creating a $TM_{01}$ mode at the frequency of the applied microwave energy and having a dielectric filling of value greater than the target. Another example is US 2008/0314894 which describes a dielectric heating applicator having a cylindrical metal body filled with a low loss dielectric material operating a $TM_{01}$ mode to be used to launch microwave energy into tissue in direct contact with the applicator.

Many devices exist that couple or feed energy from electrical coaxial structures into waveguide structures however the theory of transverse electric (TE) and transverse magnetic (TM) mode launch techniques has long been established in the literature as fundamental elements of microwave components such as dielectric filled waveguides and dielectric loaded antennas.

Traditionally in any waveguide structure including dielectrically filled waveguides a feed mechanism will include a coupling element (typically a coaxial centre conductor) which is placed into the waveguide to excite a particular electromagnetic mode as supported by the waveguide dimensional properties, an example being U.S. Pat. No. 3,128,467. In addition to the waveguide properties the mode selection depends upon the geometry of the coupling structure, for example an electrically grounded coaxial loop creates a magnetic field that can be used to excite the transverse electric (TE) mode, examples being U.S. Pat. No. 3,942,138 and U.S. Pat. No. 3,128,467 and a radiating coaxial probe creates electric fields that can be used to selectively couple into the transverse magnetic (TM) mode examples being U.S. Pat. No. 4,392,039 and U.S. Pat. No. 3,087,129. Although these techniques are well known there is novelty in the fabrication method to create these TE and TM mode coupling mechanisms by the current method.

In some applications it is desirable to physically reduce the dimensions of a waveguide such as the cross-sectional area. As the operational frequency is related to the physical dimensions this can change the frequency performance of the waveguide, with smaller cross-section typically accommodating modes at higher frequencies. As it is often desired to maintain the same operational mode or frequency a common technique is to load the waveguide with a dielectric filling thus restoring the operational frequency to the original position.

The coupling elements or structures are also placed into the dielectric medium which is often a high dielectric electroceramic material. This necessitates the machining of holes in the ceramic to accept the probes or conductive loops which can be expensive and impractical in high volume manufacture.

Another limitation is that any air gap between a conductor and the dielectric can affect the microwave operating performance unless it has been sufficiently accommodated in the design and controlled in the manufacture by tuning. Air gaps also allow the formation of high order modes and in high power applications can create a source of breakdown causing arcing and burning of the ceramic or electrode. The effect of air-gaps are particularly relevant if the Epsilon Relative (Er) value of the dielectric is much greater than that of the surrounding air (Er 1) such as in high dielectric ceramic Er 10, Er 20 Er 40 etc. In dielectric loaded waveguides the ceramic filling must be manufactured to a high accuracy to ensure a good consistence of contact with the conductive walls or stable dimensions of air filed regions to ensure accurate performance. It is common practice to add tuning elements to negate the effects of the air gaps created by manufacturing tolerances. This tuning involves the placement of capacitive or inductive elements such as metallic or dielectric tuning materials to counteract the effects on performance created by the air regions. This is often a time consuming and skilled process that dramatically increases the cost of the product.

One of the limitations of these types of dielectric filled waveguide launch mechanisms is the operational bandwidth of feed network is typically limited by the length of the coupling probes which operate over specific frequency ranges. This limitation can be improved by using the mismatch between the waveguide and the target to cancel with the mismatch between the feed mechanism and the dielectric loaded waveguide.

Another factor is that coaxial microwave components require a conductive electrical attachment mechanism which usually takes the form of a pin (male) and socket (female). In the case of a dielectric waveguide feed a pin or socket is placed within the dielectric material to facilitate connection to an external coaxial feed. This arrangement is difficult to fabricate as most highly conductive metals are not compatible with the high temperatures present during the ceramic sintering process (typ. 1300° C.+) and would require to be added after the ceramic is fired, at which point the hardened ceramic is difficult and expensive to machine.

Another factor in using pin/socket arrangements is that they possess a finite lifetime of connections becoming worn by repeated friction. This is a particular problem in microwave applications as small dimensional changes can have a detrimental effect upon microwave performance.

It is known to use self biasing pins ("pogo pin" or Z-pin) that can accommodate repeated mating cycles in different technical areas, for example as coaxial connections between a connector and circuit board as described in U.S. Pat. No. 6,822,542 and as a plug component in a coaxial connector as can be found in U.S. Pat. No. 7,922,529.

In medical applications the cost of manufacture and lifetime of a reusable part is of importance and it can be prohibitively expensive to create disposable microwave grade components for this market using traditional manufacture techniques such as bulk machining, drilling etc.

For microwave applicators manufactured using these methods a hole would have to be machined into the ceramic material with a separate metallic part being added to create the assembled component. This often necessitates a separate tuning mechanism or a number of iterations to ensure that a reliable design is achieved. As this involves labour this is an expensive method for mass production.

SUMMARY OF THE INVENTION

In a first aspect of the invention there is provided a method of forming a microwave applicator comprising forming a body comprising dielectric material and depositing conductive material on the dielectric material.

The method may comprise forming the body so that there is a void in the dielectric material. The method may comprise introducing conductive material in the void, for example by depositing conductive material in the void. The conductive material deposited in the void may be deposited such as to form a feed mechanism to couple energy into the dielectric material.

The method may comprise performing a deposition process, for example a coating or plating process to deposit the conductive material on the dielectric material and/or in the void.

By depositing the conductive material it may be ensured that there is no air gap between the conductive and dielectric material. That can eliminate a requirement for additional tuning to compensate for any air gaps, as the air gaps do not exist and therefore their influence does not need to be accommodated in the design. That can substantially reduce manufacturing costs, and improve efficiency of operation.

The deposition process may comprise at least one of an ion vapour deposition process, a sputtering process, a kiln co-fired ceramic plating process, a vacuum deposition process, an electroplating process or a solder reflow process. Alternatively or additionally a solid filling can be employed to fill the void. The conductive material may comprise at least one of silver, gold, nickel or an alloy thereof.

The use of a kiln co-fired process may ensure that a conductive paste flows and adheres to a surface of the dielectric without an air gap.

The method may comprise depositing the conductive material so that there is substantially no air gap between the dielectric material and the conductive material. The method may comprise depositing the conductive material so that the conductive material is in direct contact with the dielectric material.

The method may comprise substantially filling the void with the conductive material. That can provide a mechanical contact of greater strength or resilience for a contactor to touch.

The method may comprise forming the body using an injection moulding process. The injection moulding process may comprise injection moulding the dielectric material.

Thus, lower cost and more efficient manufacture may be obtained, particularly when manufacturing large numbers of applicators.

The microwave applicator may be formed to be releasably attachable and/or detachable to a coupling for applying electromagnetic radiation to the applicator, for example for applying electromagnetic radiation via the feed mechanism. The void and the conductive material may be configured so that, when the coupling is attached to the microwave applicator there is at least one substantially continuous electrically conductive path between the coupling and the dielectric material via the conductive material. The at least one substantially continuous electrically conductive path may comprise substantially no air gap.

The method may comprise depositing first conductive material on the surface of the void, for example to create a hollow and/or thin wall conductor. The method may comprise depositing within the void second conductive material of different type to the first conductive material.

The method may comprise depositing conductive material on an outer surface of the body, for example on an outer surface of the dielectric material, for example to create a waveguide ground plane.

The method may comprise installing the body inside a holder.

The feed mechanism may comprise a TM mode feed, which may comprise for example the conductively coated or filled void.

The feed mechanism may comprise the conductively coated or filled void, which may be configured to enter one plane and exit another, for example to link the or a conductor to the or a waveguide ground plane, which may produce a TE mode feed.

The method may comprise forming a conductive link from the conductive material deposited in the void to the conductive material deposited on the outer surface. The conductive link may comprise a tab and/or may affect the frequency performance of the feed mechanism. The method may comprise forming the conductive link by depositing conductive material, for example on an end face of the body. The depositing of the conductive material may comprise at least one of etching, patterning, printing, sputtering, vacuum deposition, ion vapour deposition.

The conductive link, for example the tab, may comprise a discontinuity which may act as a capacitive coupling. The capacitive coupling may affect the high frequency connection to the waveguide ground plane and/or may prevent a direct current (DC) path.

An electrical connection, for example the conductive link, may be used to couple between a ground and a probe element on the outside of the structure as opposed to placing them inside the ceramic. That can be achieved by the previously described coating methods or by using silk screening to create specific geometries to avoid fully coating a surface.

In another independent aspect of the invention there is provided a method of forming a coupling to a dielectrically filled microwave applicator comprising forming a feed probe electrical connection; forming a waveguide electrical connection, wherein the feed probe electrical connection may be a connecting element that mechanically and electrically contacts an applicator feed (or centre conductor) and the waveguide electrical connection may be a connecting element that mechanically and electrically contacts an outer surface (or waveguide ground).

In a further independent aspect of the invention there is provided a method of forming a microwave applicator comprising forming a first waveguide comprising first dielectric material, forming a second waveguide comprising second dielectric material and forming at least one feed mechanism for coupling energy into the dielectric material into the first and/or second waveguide.

The first waveguide may be arranged to couple energy into the second waveguide or vice versa.

The first dielectric material may be different from the second dielectric material and/or the first waveguide may be of a different shape and/or size than the second waveguide. The method may comprise forming the first waveguide and/or the second waveguide using an injection moulding process. The injection moulding process may comprise injection moulding the first and/or second dielectric material. The first dielectric material may be the same as the second dielectric material. The method may comprise forming a waveguide body comprising a first section having a first shape and/or size and a second section having a second shape and/or size. The first section may comprise or form part of the first waveguide and the second section may comprise or form part of the second waveguide. The waveguide body may be formed by injection moulding the dielectric material into a mould.

The first waveguide may be designed to communicate electromagnetic energy from the feed to the second waveguide by supporting an electromagnetic mode.

The second waveguide may be configured to communicate electromagnetic energy from the first waveguide to the target.

The second waveguide may be configured to act as an impedance transformer to transform a target impedance to that of the first waveguide.

The second waveguide may be configured to present a mismatch from a target impedance to the first waveguide.

The second waveguide may be configured to present a mismatch to the first waveguide.

The first and second waveguide may be configured to present a mismatch to the feed mechanism to cancel a portion of the mismatch of the feed mechanism.

The first and second waveguides may be configured to present a mismatch to the feed mechanism that occurs at a frequency different to the operating frequency of the feed mechanism thus increasing operating bandwidth.

The method may comprise forming a plurality of waveguides, for example to provide a plurality of mismatches each occurring at a different frequency to provide increasing operating bandwidth. The method may comprise forming the plurality of waveguides in a stepped structure. Each waveguide may have a different shape and/or size.

According to a further independent aspect of the invention there is provided a microwave applicator comprising a body that comprises dielectric material including a void in the dielectric material, and conductive material deposited in the void to form a feed for coupling energy into the dielectric material.

The conductive material may comprise material deposited by a coating or plating process to deposit the conductive material on the dielectric material.

There may be substantially no air gap between the dielectric material and the conductive material. The conductive material may be in direct contact with the dielectric material.

The conductive material may be deposited on the surface of the void, for example to create a hollow and/or thin wall conductor.

The applicator may comprise a second conductive material within the void of a different type of material to the first conductive material.

The applicator may comprise conductive material on an outer surface of the body, for example on an outer surface of the dielectric material, which may form a waveguide ground plane.

The applicator may comprise a conductive link from the conductive material in the void to the conductive material on the outer surface.

The conductive link may comprise a tab. The conductive link may affect the frequency performance of the feed mechanism.

The conductive link may comprise deposited conductive material. The conductive link may comprise conductive material on an end face of the body.

The conductive link may comprise a capacitive coupling.

The capacitive coupling may affect the high frequency connection to the waveguide ground plane and/or may prevent a direct current (DC) path to the waveguide ground plane.

The conductive link may include a discontinuity, which for example provides the capacitive coupling.

The void may be substantially filled with conductive material. The body may be injection moulded. The dielectric material may be injection moulded.

The conductive material may comprise at least one of silver, gold, nickel or an alloy thereof.

The microwave applicator may be releasably attachable and/or detachable to a coupling for applying electromagnetic radiation to a waveguide component of the applicator via the feed mechanism.

In a further aspect of the invention there is provided a plurality of the microwave applicators, each having different frequency transmission characteristics, and each releasably attachable and/or detachable to the coupling.

The void and the conductive material may be formed so that, when the coupling is attached to the microwave applicator there is at least one substantially continuous electrically conductive path between the coupling and the dielectric material via the conductive material.

The at least one substantially continuous electrically conductive path may comprise substantially no air gap.

The applicator may comprise a housing, and/or the microwave applicator may comprise substantially no tuning components for tuning frequency.

The feed mechanism may comprise a TM mode feed.

The feed mechanism may be configured to enter one plane and exit another, to link the conductive material to the or a waveguide ground plane.

According to a further, independent aspect of the present invention, there is provided an apparatus for use as a microwave applicator comprising:
a ceramic dielectric material;
at least one feed mechanism to couple energy into the ceramic material;
a waveguide to sustain an electromagnetic mode.

The ceramic dielectric material may be of any suitable form such as rectangular or cylindrical or any other shape that can support an electromagnetic mode either propagating (radiating) or resonant (stored) and of any dielectric property value.

The ceramic dielectric material may be formed by being machined from a bulk solid or by being injection molded, to contain holes (blind or penetrating) or features to accept conductors required for a feed mechanism.

The feed mechanism may be formed by a plating or coating process such as ion vapour depositing, sputtering or vacuum deposition of conductive metals such as silver, gold, nickel or any other conductive metal to coat the interior of the holes to create conductive features that adhere directly to the surrounding dielectric material without air gap.

The feed mechanism may also be formed by depositing a metal in liquid state such as silver, gold, nickel, solder or other conductive coating or filling including any conductive metals, conductive epoxy composites or conductive paints or coatings to cover the interior surface of the holes to create a conductive layer that adheres directly to the dielectric material without air gap. The conductive material depth should be substantial enough to accommodate the required electromagnetic skin depth to support surface electrical currents at microwave frequencies.

The conductive material may be applied to the interior surface only to create a hollow "thin wall" conductor or may be applied in single or multiple applications to partially or entirely fill the void of the hole to create a solid conductor.

Separately a secondary conductive filling of a different material may be introduced to join with the primary "thin wall" conductor to entirely fill the void to create a solid conductor.

The outer surfaces of the ceramic component may be coated in a conductive material to generate the waveguide ground plane negating the requirement for a conductive holder or alternatively negating the requirement for applying a conductive foil jacket to support the waveguide mode. A conductive or insulating support holder may also be used in conjunction with this technique to enhance the mechanical strength if required. Where there are transitions in diameter in the outer walls these may be tapered to improve the adhesion of the metallic coating to the surface.

The feed mechanism may comprise a conductively coated or filled blind hole to create a TM mode feed probe.

It may also be a conductively coated or filled penetrating hole that enters one face and exits another to create a path between the centre conductor and the waveguide ground plane to create a TE mode feed.

In particular embodiments, the TE mode feed may be connected directly to the waveguide ground plane via a conductive body or "tab" patterned, etched, printed or deposited onto the end face surface of the ceramic waveguide containing the feed probe.

The tab may be of any length or shape that may affect the frequency performance of the feed mechanism.

The tab may be connected directly to the feed probe or may have a discontinuity along its length acting as a capacitive coupling effecting the high frequency connection to the waveguide ground plane.

According to a further independent aspect of the present invention there is provided an apparatus for use in coupling to a dielectrically filled microwave applicator comprising:
 a feed probe electrical connection;
 a waveguide electrical connection.

The feed probe electrical connection may be a connecting element that mechanically and electrically contacts to the applicator feed.

The waveguide electrical connection may be a connecting element that mechanically and electrically contacts the applicator waveguide (also called the outer body or waveguide ground).

The feed probe electrical connection may be formed by a self biasing pin, conductive spring, conductive elastomer or other self biasing electrical contact. A pogo pin such as a MILL-MAX 0906 Spring-Loaded Pogo Pin may be used for example. The use of a self-biasing pin to connect to a dielectric waveguide feed in a microwave applicator can provide a quick, reliable connection to the microwave applicator without excessive connect/disconnect forces, and can enhance connection lifetime whilst accommodating manufacturing tolerances.

The waveguide electrical connection may be formed by a conductive sleeve that accepts the waveguide and makes electrical contact with the conductive outer coating of the waveguide. The sleeve could comprise an array of sprung contactors arranged to accommodate a waveguide being inserted and able to accommodate manufacturing and alignment tolerances by being flared.

At least part of the waveguide electrical connection device may be fabricated from heat treated brass, beryllium copper, or another hardened metal and may be coated with gold, silver or nickel to ensure good long-term electrical contact.

According to a further, independent aspect of the present invention there is provided an apparatus for use as a microwave applicator comprising.
 a ceramic dielectric material;
 at least one feed mechanism to couple energy into the ceramic material;
 a first waveguide to sustain an electromagnetic mode;
 a second waveguide region of different dimension to the first.

The feed mechanism may be designed to couple energy into the first waveguide.

The first waveguide may be designed to communicate electromagnetic energy from the feed to the second waveguide by supporting an electromagnetic mode.

The second waveguide may be designed to communicate electromagnetic energy from the first waveguide to the target.

The second waveguide may be designed to act as an impedance transformer to transform the target impedance to that of the first waveguide.

The second waveguide may be designed to present a mismatch from the target impedance to the first waveguide.

The second waveguide may be designed to present a mismatch to the first waveguide.

The first and second waveguide may be designed to present a mismatch to the feed mechanism to cancel a portion of the mismatch of the feed mechanism.

The first and second waveguide may be designed to present a mismatch to the feed mechanism that occurs at a frequency different to the operating frequency of the feed mechanism to enhance the operating bandwidth.

A number of waveguide steps of various dimensions may be employed using the aforementioned technique to provide a plurality of mismatches each a different frequency corresponding to each waveguide dimension to provide increased operating bandwidth.

In another independent aspect of the invention there is provided a microwave applicator comprising:
 a dielectric material containing a void;
 a conductive filling introduced into the void to create a feed mechanism to couple energy into the dielectric material; and
 a waveguide region to sustain an electromagnetic mode.

The dielectric material may be of any regular shape such as rectangular or cylindrical or any other shape supporting an electromagnetic mode of either propagating (radiating) or resonant (stored) where the dielectric material is of any dielectric property value.

The dielectric material may be formed by being machined or injection molded to contain a void such as a hole (blind or penetrating).

The feed mechanism may be formed by a plating or coating process such as ion vapour depositing, sputtering or vacuum deposition of conductive metals such as sliver, gold, nickel or other conductive metals to coat the interior of the void creating a conductive feature that adheres directly to the surface of the dielectric material without air gap.

The feed mechanism may be formed by depositing a metal in liquid state such as silver, gold, nickel, solder or other conductive coating or filling including any conductive metals, conductive epoxy composites or conductive paints or coatings.

The deposited conductive material thickness may accommodate the required electromagnetic skin depth to support surface electrical currents at microwave frequencies.

The conductive material may be applied to the interior surface to create a hollow "thin wall" conductor.

The conductive material may be applied in single or multiple applications to partially or entirely fill the void of the hole to manufacture a solid conductor.

A secondary conductive filling of different type may be applied to join with the primary "thin wall" conductor to entirely fill the void to create a solid conductor.

The outer surfaces of the dielectric material may be coated by a plating or coating process such as ion vapour deposition, sputtering or vacuum deposition of conductive metals such as silver, gold, nickel or other conductive metals to adhere directly to the outer surface of the dielectric material without air gap to create a waveguide ground plane.

The microwave applicator may be installed inside a conductive or insulating support holder to enhance mechanical strength.

The feed mechanism may comprise a conductively coated or filled blind hole creating a TM mode feed.

The feed mechanism may comprise a conductively coated or filled penetrating hole that enters one plane and exits another to link the centre conductor to the waveguide ground plane to produce a TE mode feed.

The link to the waveguide ground plane may be via a conductive body or "tab" patterned, etched, printed or deposited onto the end face surface of the waveguide containing the feed probe. The tab may be of any length or shape that effects the frequency performance of the feed mechanism.

The tab may have a discontinuity along its length acting as a capacitive coupling effecting the high frequency connection to the waveguide ground plane and preventing a direct current (DC) path.

In a further independent aspect of the invention there is provided a coupling means to a dielectrically filled microwave applicator comprising:
    a feed probe electrical connection;
    a waveguide electrical connection;
        wherein the feed probe electrical connection may be a connecting element that mechanically and electrically contacts the applicator feed (or centre conductor) and the waveguide electrical connection may be a connecting element that mechanically and electrically contacts the outer surface or (waveguide ground)

The feed probe electrical connection may be formed by a self biasing pin, conductive spring, conductive elastomer or other self biasing electrical contact.

The waveguide electrical connection may be formed by a conductive sleeve to accept the waveguide and make electrical contact with the conductive outer surface of the waveguide.

An array of sprung contactors may be arranged to accommodate the waveguide being inserted capable of accommodating manufacturing and alignment tolerances by being flared.

The waveguide electrical connection device may be fabricated from heat treated brass, beryllium copper, or another hardened metal and coated with gold, silver or nickel.

In another independent aspect of the invention, there is provided a microwave applicator comprising
    a dielectric material;
    at least one feed mechanism to couple energy into the dielectric material;
    a first waveguide containing dielectric material to sustain an electromagnetic mode;
    a second waveguide region containing dielectric material of different dimension to the first.

The microwave applicator may possess a feed mechanism designed to couple energy into the first waveguide.

The first waveguide may be designed to communicate electromagnetic energy from the feed to the second waveguide by supporting an electromagnetic mode.

The second waveguide may be designed to communicate electromagnetic energy from the first waveguide to the target.

The second waveguide may be designed to act as an impedance transformer to transform the target impedance to that of the first waveguide.

The second waveguide may be designed to present a mismatch from the target impedance to the first waveguide.

The second waveguide may be designed to present a mismatch to the first waveguide.

The first and second waveguides may be designed to present a mismatch to the feed mechanism to cancel a portion of the mismatch of the feed mechanism.

The first and second waveguides may be designed to present a mismatch to the feed mechanism that occurs at a frequency different to the operating frequency of the feed mechanism thus increasing operating bandwidth.

A number of waveguide steps of various dimensions may be employed to provide a plurality of mismatches each occurring at a different frequencies corresponding to each waveguide dimension to provide increasing operating bandwidth.

There may also be provided an apparatus or method substantially as described herein with reference to the accompanying drawings.

Any feature in one aspect of the invention may be applied as a feature in any other aspect of the invention, in any appropriate combination. For example, apparatus features may be applied as method features and vice versa.

BRIEF DESCRIPTION OF THE DRAWINGS

These and other aspects of the present invention will now be described, by way of example only, with reference to the accompanying figures, in which:

FIG. 2 shows diagrammatic cross sectional views of electric and magnetic coupling feeds realizable in hollow plated and filled plated configurations;

FIG. 11 displays a dimensioned drawing of the ceramic microwave applicator part.

DETAILED DESCRIPTION

Certain embodiments as disclosed herein provide for a microwave applicator that incorporates a probe feed for the transmission of energy from a coaxial feed into a dielectric filled waveguide and ultimately into a target.

Various arrangements are provided in the different embodiments, after reading the description, it will become apparent to one skilled in the art that various changes and modifications can be made, and equivalents or alternative embodiments employed. However, although various embodiments of the present invention will be described herein, it is understood that these embodiments are presented by way of example only and should not be construed to limit the scope or breadth of the present invention as set forth in the appended claims.

Figure 1:
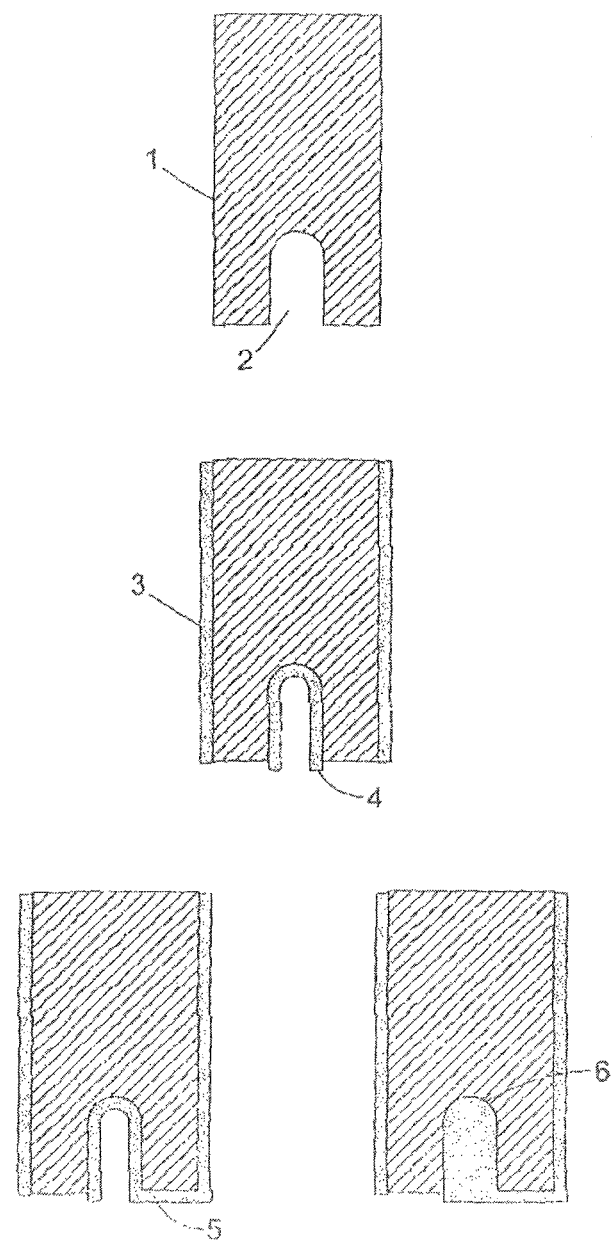
FIG. 1 illustrates a series of diagrammatic cross sectional views of the ceramic plating process.

With reference initially to FIG. 1 of the drawings, there are described process steps required to fabricate a probe from a dielectric body 1.

In the embodiment of FIG. 1, the dielectric probe is formed using an injection moulding process. Any other suitable method for forming the body can be used in other embodiments.

A void 2 is initially introduced into the dielectric body. The void 2 in the embodiment of FIG. 1 is formed as part of the injection moulding process, but in alternative embodiments the void be formed by drilling, erosion, or any other suitable forming technique.

A conductive coating, covering or plating 3 is introduced to the outside surface of the dielectric body to act as an electromagnetic waveguide. The conductive coating, covering or plating can function as a waveguide ground plane, depending on the configuration of the device in use. A conductive coating, covering or plating is also deposited onto the interior surface of the void to create a hollow conductor 4. In the embodiment of FIG. 1 the conductive material is gold, but any suitable conductive material can be used in other embodiments, for example silver, gold, nickel or an alloy thereof.

In the embodiment of FIG. 1, the conductive coating is deposited onto the interior surface of the void and onto the outside surface of the dielectric body using a kiln co-fired ceramic plating process. In subsequent operation, the hollow conductor 4 effectively acts like a probe that can be used to launch electromagnetic waves into the ceramic waveguide.

It is a feature of the embodiment of FIG. 1 that the conductive material deposited into the void to form the hollow conductor 4 is deposited so that there is substantially no air gap between the dielectric material and the conductive material and data material is in direct contact with the dielectric material.

In applications where a TE mode is to be launched a known method is to employ a magnetic coupling, realised by shorting the centre conductor to the waveguide wall. In the embodiment of FIG. 1, this is achieved by providing a connection 5 comprising conductive material between the hollow conductor 4 and the conductive material providing the waveguide wall 3. An electrically conductive material is painted, coated, silk screened, etched or deposited by any suitable method onto the end face of the dielectric body 1 to create the connection 5.

In the embodiment of FIG. 1, the connection 5 comprises a tab that includes a conductive discontinuity that provides capacitive coupling between the conductive material deposited in the void and the conductive material deposited on the outer surface. In this case, the capacitive coupling in operation affects the high frequency connection to the waveguide ground plane provided by the conductive material 3 on the outer surface of the dielectric material, and/or prevents a direct current (DC) path to the waveguide ground plane.

In final stages of manufacture, the dielectric body is installed in an outer housing, also referred to as a holder, formed for example of plastic, which provides an insulating arrangement around the outer conductive layer 3. In the embodiment of FIG. 1, the resulting microwave applicator is a disposable component for medical applications that can be provided for single-use or a limited number of uses. The applicator in this case can be connected to a probe feed apparatus in turn comprising or connected to a microwave source. The applicator in this embodiment does not include any frequency tuning components and tuning, if any, can be performed by tuning components of the separate probe feed apparatus or microwave source. By limiting the components included in the microwave applicator (in the case of FIG. 1 to a dielectric body, deposited conductive material and an outer housing) and by using techniques such as injection moulding and deposition processes, a particularly efficient method of mass producing or otherwise manufacturing microwave applicators can be provided.

In the embodiment of FIG. 1, each of the regions 3, 4, 5 of conductive material can be deposited in a single deposition process, for manufacturing efficiency, if so desired, but often the deposition process will be repeated to deposit the different regions.

The conductor thickness can be selected in dependence upon current carrying requirements and operating frequency. The conductive coating can be formed to be continuous and to not contain holes or excessively thin regions to avoid electrical breakdown (sparking).

To fulfil other requirements such as supporting higher currents, or mechanical connection it can be desirable to fill the hollow conductor 4 with a conductive or other filling 6, as shown schematically in FIG. 1. The conductive filling 6 can be of the same or different material to the material of the deposited layer 4. The materials can be selected to provide desired electromagnetic and mechanical characteristics.

It will be understood that embodiments are not limited to the particular arrangement shown in FIG. 1. FIG. 2 shows microwave applicators 7, 8, 9, 10, 12, 13 in various other embodiments, namely a coated probe 7, filled coated probe 8, shorted coated probe 9, shorted filled coated probe 10, coated conductive loop 12 and filled coated conductive loop 13. In each case, dielectric material is shown by hatched areas and conductive material is shown by solid black areas.

Figure 3:
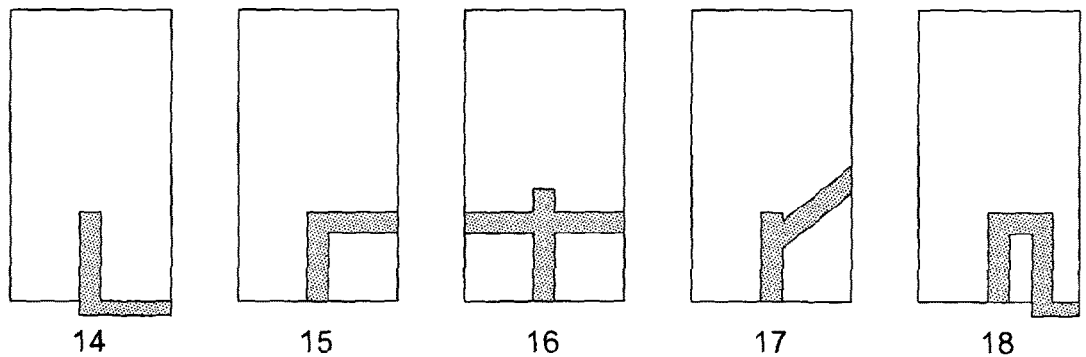
FIG. 3 is a number of diagrammatic cross sectional views of magnetic coupling feed configurations.

The conductive link between the void conductive material and the conductive material on the outer surface is not limited to the arrangement of FIG. 1 and any suitable conductive link can be used. A small number of possible conductive links in the form of magnetic feed coupling configurations in alternative embodiments are illustrated in FIG. 3, for example an end-coupled probe 14, side-coupled probes 15, 17, loop 18 and T bar-coupled probe 16. In FIG. 3, the boundary of the dielectric material is shown by the rectangular shape and the conductive link is shown by solid black areas. The outer conductive coating is not shown for clarity but would be present along each of the long sides of the rectangular shape.

Figure 4:
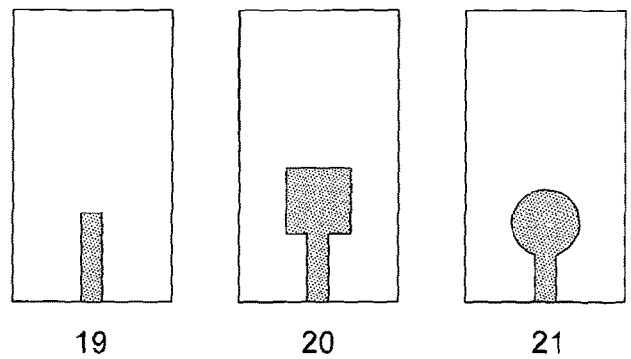
FIG. 4 illustrates diagrammatic cross sectional views of electric coupling feed configurations.

In FIG. 4 various configurations of the void filled with conductive material forming an electric probe, according to alternative embodiments, are shown, namely a standard probe 19, top-hat probe 20, and spherically-tipped probe, 21. The conductive material within the void is again shown by solid black areas and the boundary of the dielectric material is shown by the rectangular shape.

Figure 5:
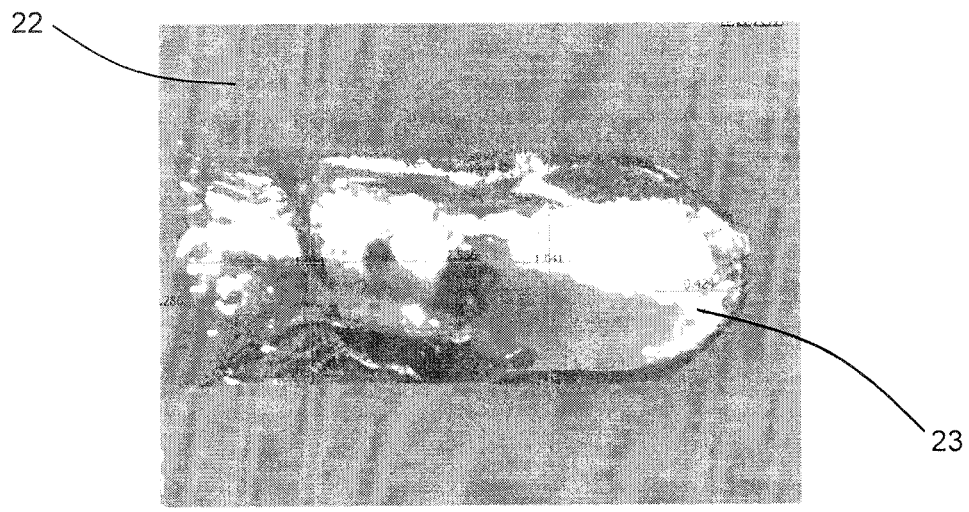
FIG. 5 shows a photograph of a cross section of an embodiment of a plated probe inside a ceramic body.

A photograph of a cross section of an embodiment of a plated probe is displayed in FIG. 5. In this image the probe void has been molded into the surrounding dielectric 22. A conductive silver plating 23 has been introduced onto the interior walls of the void to form a hollow probe. This plating or coating is at least 80 microns in depth as the electrical skin depth at 8 GHz is 72 microns for pure Silver (resistivity =1.59 $\mu\Omega$-cm).

Figure 6:
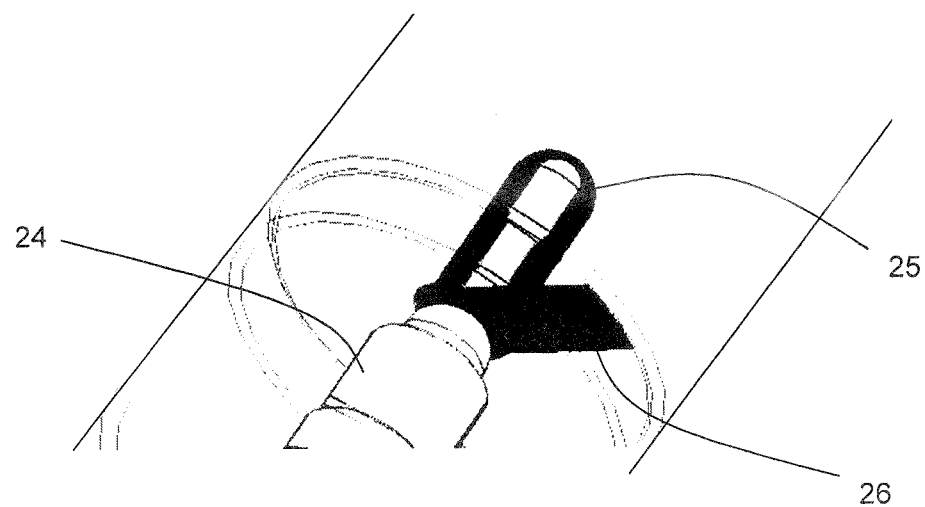
FIG. 6 shows a diagrammatic illustration of self biasing pin contacting a plated magnetic coupling probe feed arrangement.

FIG. 6. shows an embodiment of a connection means between a coaxial feed line and a shorted probe feed. In this embodiment a MILL-MAX 0906 Spring-Loaded Pogo Pin 24 contacts against a plated probe 25 incorporating a rectangular connection tab 26 that provides an electric contact between the probe and the conductive outer waveguide wall. In this instance the spring loaded pin is surrounded by air as part of the coaxial to waveguide transition.

Figure 7:
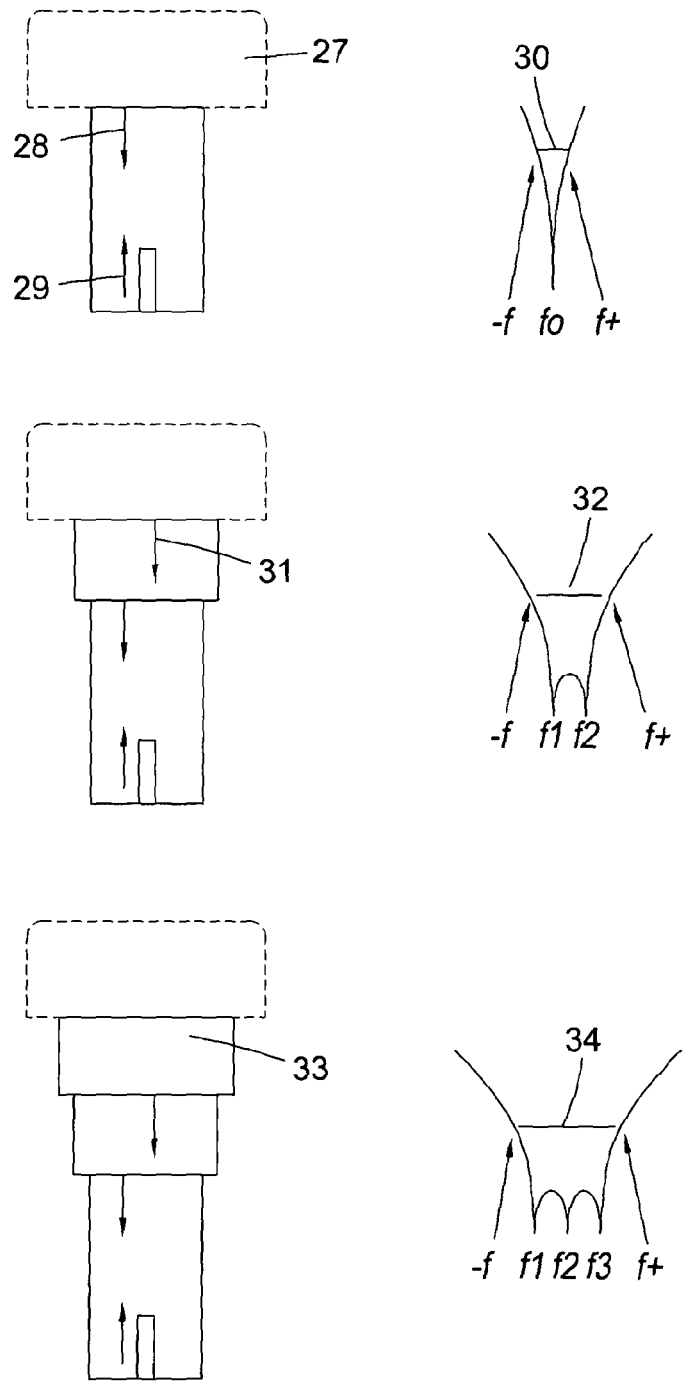
FIG. 7 shows diagrammatic cross sectional views of the effect of multiple steps in the ceramic waveguide on performance bandwidth.

With reference to FIG. 7, the effect of various waveguide steps upon the operating bandwidth is described. The target 27 to which electromagnetic radiation is to be applied may be any dielectric material such as tissue or a material having a dielectric different to the dielectric of the waveguide. The difference in dielectric creates a mismatch 28. The impedance seen by the feed 29 will partially cancel with the mismatch 28 to create a narrow operating bandwidth 30, centred upon a frequency of operation (fo) with an upper and lower band (−f, +f) which possesses a return loss or "match" typically better that −12 dB between these points. The operating frequency (fo) is related to the length of the probe and the dielectric constant of the waveguide having dimension to support the chosen mode at the required frequency. Out-with the (−f, +f) frequency ranges all the incident energy is returned back into the feed mechanism and reflected back to the source. By adding another waveguide dimension a further mismatch 31 can be introduced that will partially cancel with the impedance seen by the feed 29. This cancellation can be selected to occur at a frequency f2 different to first f1 to result in an increased operating bandwidth 32. Likewise by adding other waveguide dimensions further mismatches 33 can be created to enhance the operating bandwidth 34.

It should be noted that "waveguide dimension" may refer to a new portion with different diameter, height, width, shape, material or dielectric constant than that of the existing waveguide. It may also refer to removing or adding material to the existing waveguide such as creating a void or hole in the material or in the conductive walls or adding a conductive or dielectric material into, or onto the existing waveguide to manufacture a discontinuity to create the mismatch(s).

Figure 8:
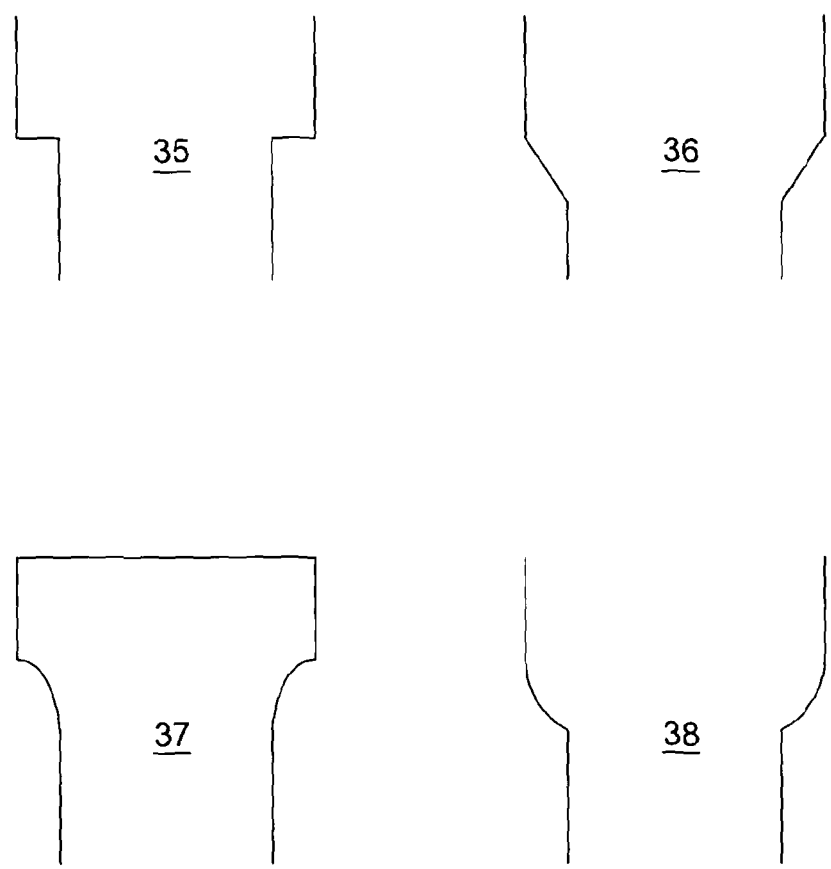
FIG. 8 illustrates diagrammatic cross sectional views of various waveguide width transitions.
Figure 9:
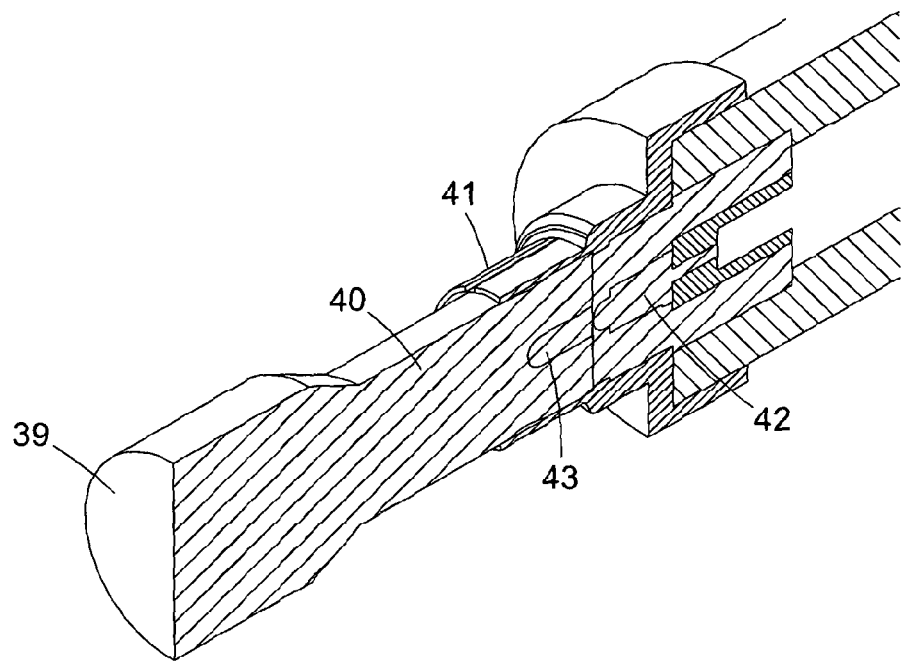
FIG. 9 displays a diagrammatic isometric view of a cross section of an embodiment of a microwave applicator.

In the case where a single dielectric material is used, for example a single one-piece dielectric body, various embodiments of possible transitions are illustrated in FIG. 8. These transitions are applicable to any shape of waveguide such as cylindrical, rectangular, elliptical, reduced height etc. and may be stepped 35, tapered 36, curved inwards 37 or curved outwards 38. It has been found that the use of a taper or curved profile, particularly when used in conjunction with a deposition process to deposit conductive material, is to reduce variation in the density or thickness of conductive material at or around the location of transition as such variation can increase the effective dielectric constant of the part. Thus, the use of a taper or curved profile can in some embodiments reduce variation or inaccuracy in electromagnetic properties. A microwave applicator for use in depositing energy into tissue according to an embodiment of the present invention is illustrated in FIG. 9. In this example a high dielectric ceramic (D37™ by Morgan Electroceramic Ltd.) was constructed with an upper waveguide 39 of length 5.3 mm and diameter 6.8 mm connected via a 2 mm tapered section to a lower waveguide 40 of length 9.2 mm and diameter 4.75 mm. The waveguide is placed into a receptacle 41 which maintains electrical continuity to the waveguide ground plane using a cylindrical arrangement of sprung metallic fingers, flared to accept the ceramic body. To reduce the cost of manufacture the receptacle 41 is designed to cap the launch mechanism and contains all the highest tolerances in one component.

Figure 10:
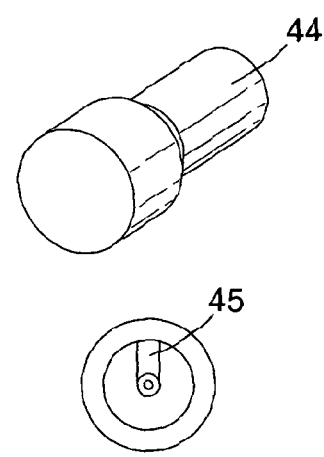
FIG. 10 displays a diagrammatic view of the external plating on an embodiment of a microwave applicator.

The internal probe 43 of length 2.5 mm and diameter 1 mm was silver plated and loaded with lead free solder to provide a mechanical dead stop for a MILL-MAX 0906 spring-loaded pogo pin 42. FIG. 10 illustrates the external plating of the ceramic component where a conductive silver plating was applied to the outer surface 44 to create the waveguide and a 1 mm wide by 3.375 mm length rectangular tab 45 is screen printed onto the lower end face to electrically short the probe to the outer waveguide ground plane for the purpose of launching a transverse electric (TE) mode.

Figure 12:
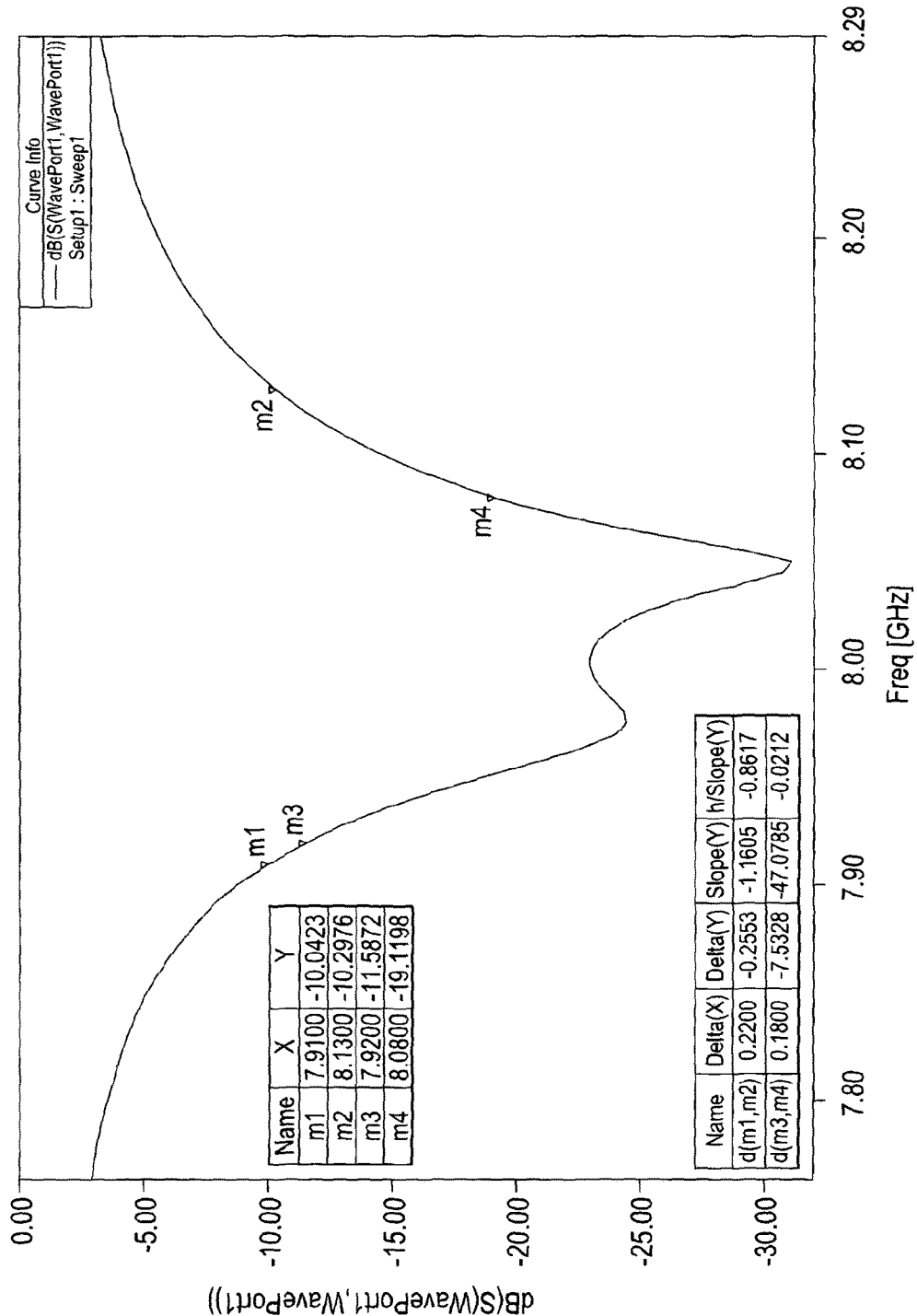
FIG. 12 displays the simulated results for an embodiment of the microwave applicator when placed against simulated tissue.
Figure 13:
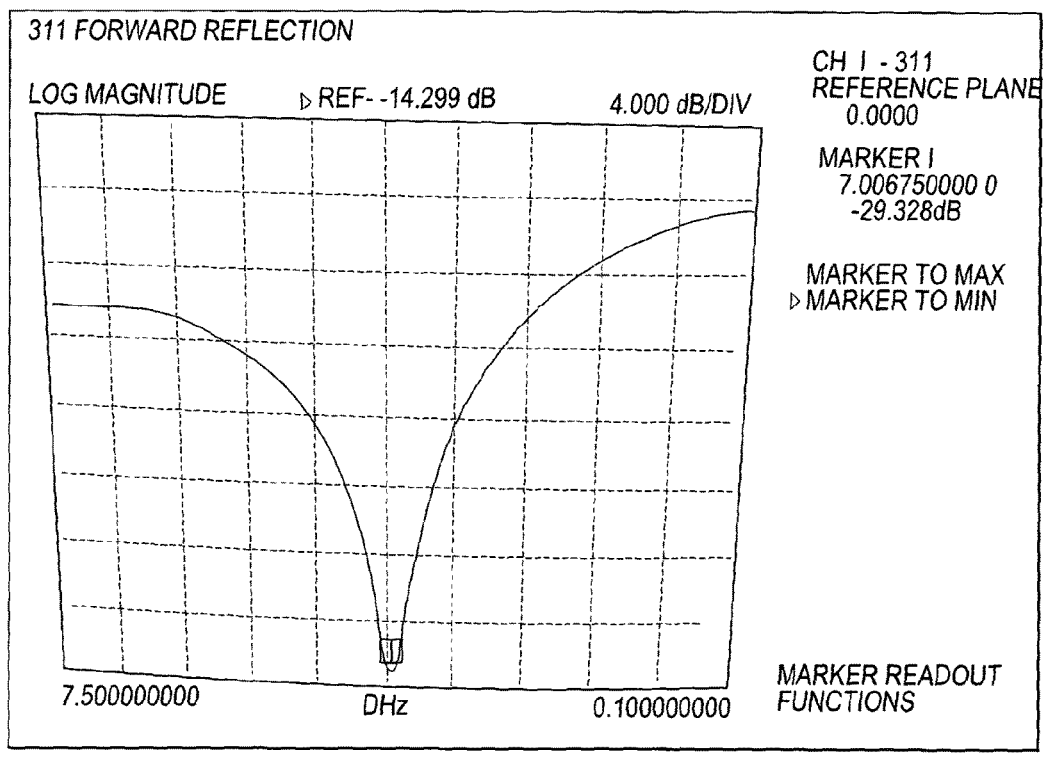
FIG. 13 displays the measured results for an embodiment of the microwave applicator when placed against tissue.

FIG. 12 illustrates the designed microwave performance of the arrangement when placed against tissue for operation at 8 GHz with greater than 150 MHz operating bandwidth. Finally, FIG. 13 is a graph representing testing results for the arrangement confirming the operation as designed.

Figure 14:
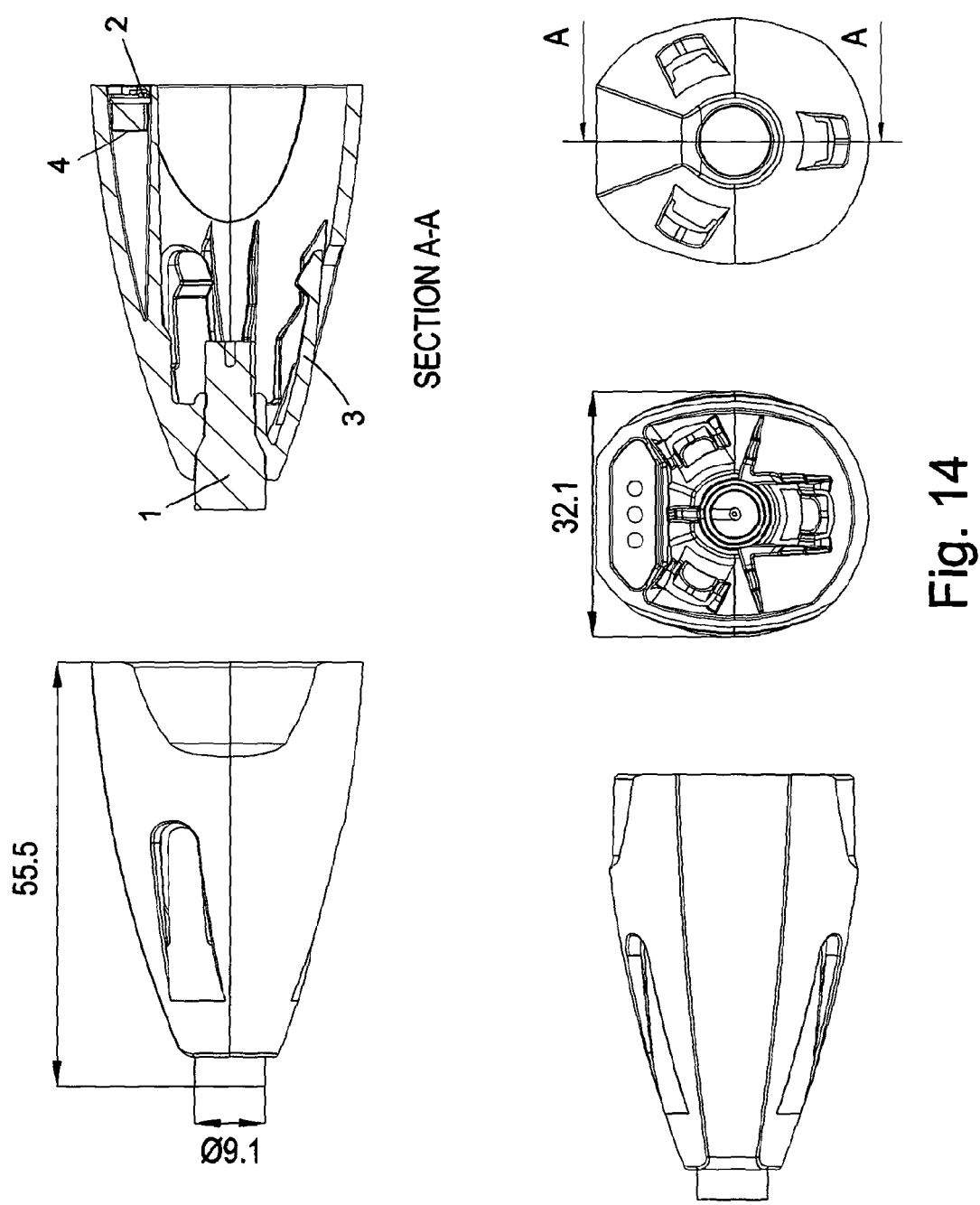
FIG. 14 displays a dimensioned drawing of the assembled disposable microwave applicator part.
Figure 15:
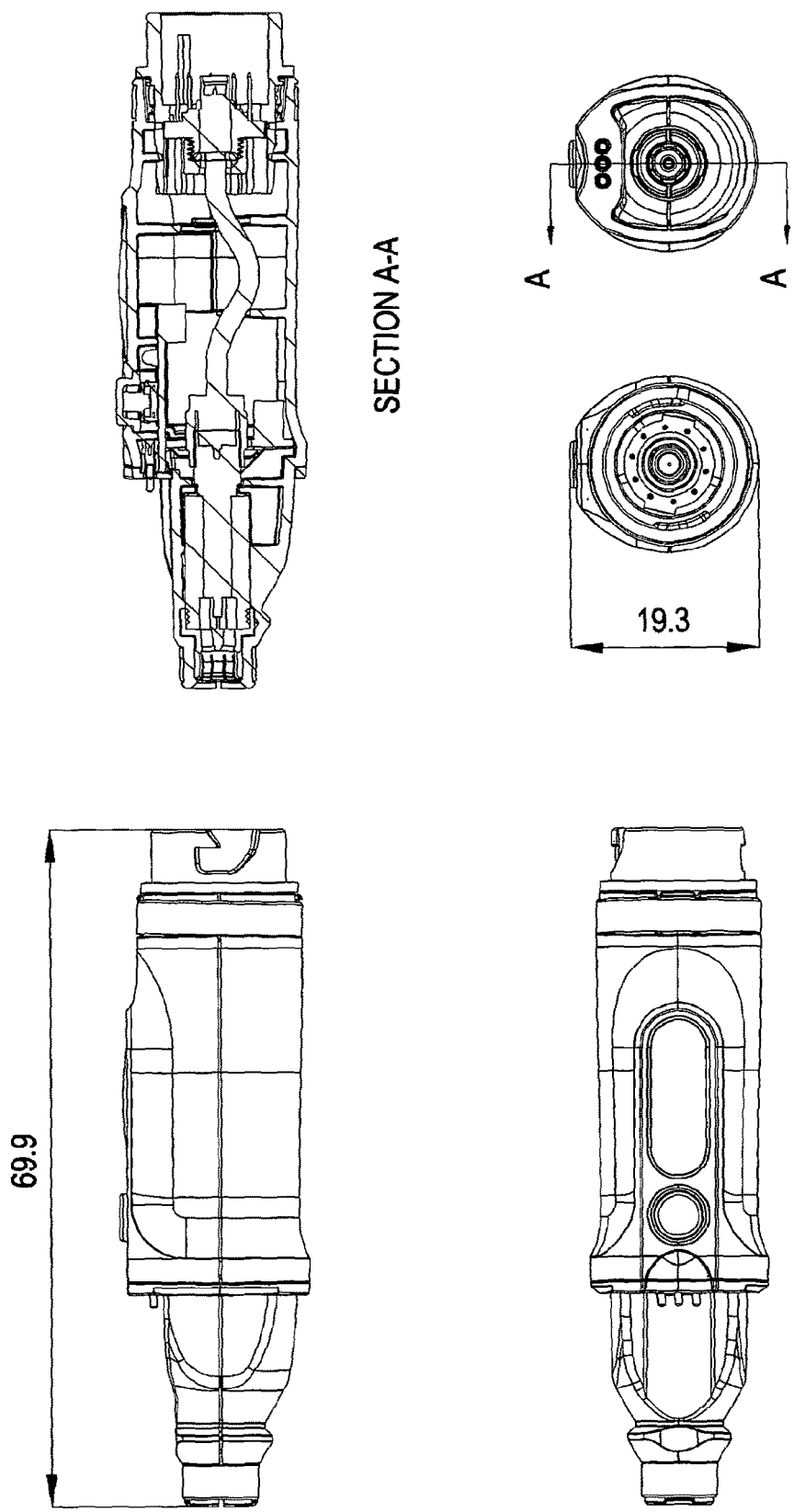
FIG. 15 displays a dimensioned drawing of the assembled reusable hand piece which connects to the microwave applicator part.
Figure 13:
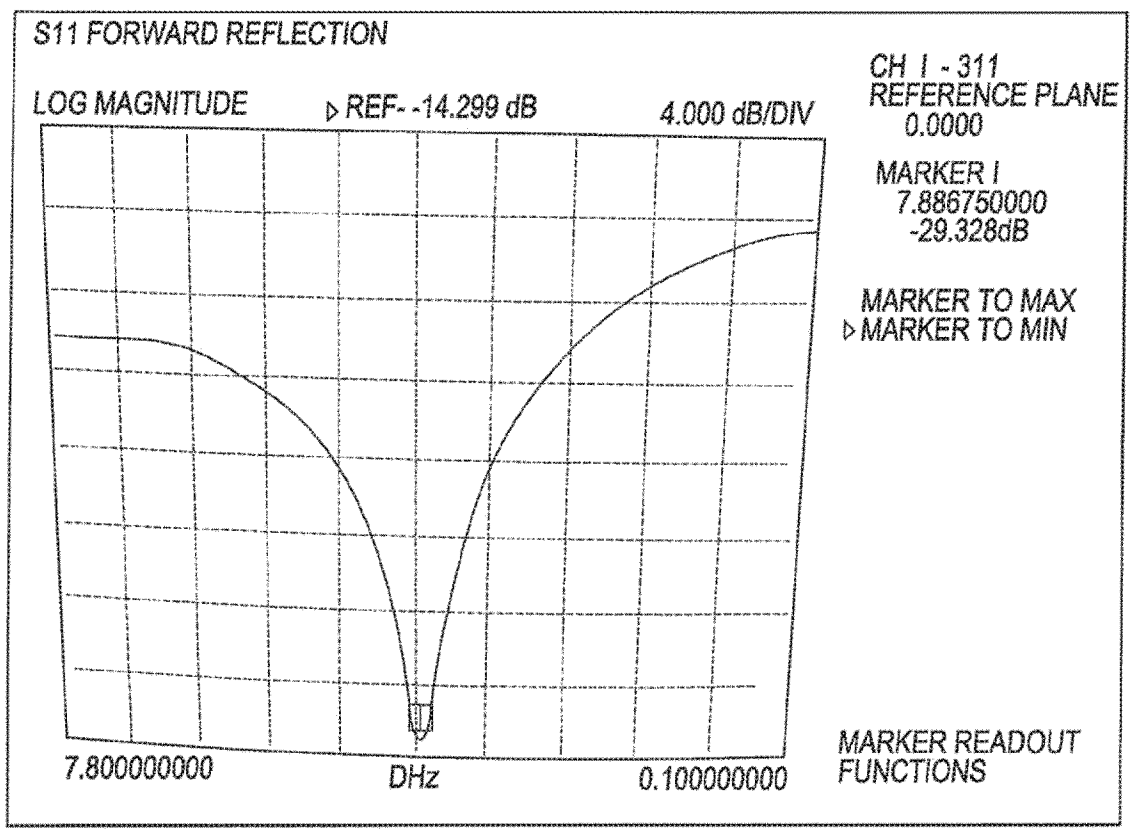

FIG. 14 is a dimensioned drawing of an assembled disposable microwave applicator part according to an embodiment. FIG. 15 is a dimensioned drawing of an assembled reusable hand piece which connects to the microwave applicator part of FIG. 14.

In the embodiment of FIG. 1, the conductive material is deposited onto the dielectric body using a kiln co-fired ceramic plating process. However, in alternative embodiments, any other suitable deposition method can be used, for example an ion vapour deposition process, a sputtering process, or a vacuum deposition process. In such alternative embodiments, the conductive material can be deposited into the void and onto the outer surfaces in a single process or, alternatively, the material can be deposited into the void and onto the outer surfaces using different techniques and/or at different stages of the process.

Embodiments can include plating, metalizing or filling of molded voids in particular blind voids to create microwave coupling structures in particular within ceramic dielectrics. The conductive coating of blind voids may be provided.

By using new manufacture techniques in conjunction with innovative microwave design, a cost effective high volume disposable microwave applicator can be realised.

It should be understood that the embodiments described herein are merely exemplary and that various modifications may be made thereto without departing from the scope of the invention.

Each feature disclosed in the description, and (where appropriate) the claims and drawings may be provided independently or in any appropriate combination.

The invention claimed is:

1. A method of forming a medical microwave applicator for use in treating tissue comprising:
    forming a body comprising dielectric material so that there is a void in the dielectric material;
    performing a deposition process to deposit conductive material in the void to partially or entirely fill the void to create a conductive feature that adheres directly to the dielectric material, the deposited directly adhered conductive feature being a probe feed that partially or entirely fills the void and that couples electromagnetic energy via the directly adhered conductive material of the probe feed into a waveguide comprising the dielectric material such that the electromagnetic energy is transmitted through the dielectric material of the waveguide to an end of the medical microwave applicator for placing adjacent to or in contact with the tissue;
    further performing the deposition process so that the directly adhered conductive material of the probe feed is deposited to have a thickness and configuration to provide a directly adhered transmission structure that receives the electromagnetic energy from a coaxial feed and transmits the electromagnetic energy through the directly adhered conductive material of the probe feed and into the dielectric material; and
    forming a conductive link from the conductive material deposited in the void to conductive material on an outer surface, the outer surface of the conductive material being configured for connection to the coaxial feed to receive the electromagnetic energy via the coaxial feed and the conductive link being arranged so as to launch the electromagnetic energy as a transverse electric (TE) mode.

2. The method according to claim 1, wherein the depositing of the conductive material comprises performing a coating or plating process to deposit the conductive material on the dielectric material.

3. The method according to claim 1, wherein the depositing comprises at least one of an ion vapour deposition process, a sputtering process, a kiln co-fired ceramic plating process or a vacuum deposition process.

4. The method according to claim 1, wherein the depositing comprises depositing first conductive material within the void.

5. The method according to claim 1, further comprising depositing conductive material on an outer surface of the body to create a waveguide ground plane.

6. The method according to claim 5, further comprising forming the conductive link from the conductive material deposited in the void to the conductive material deposited on the outer surface of the body.

7. The method according to claim 6, wherein the conductive link comprises a tab.

8. The method according to claim 6, wherein the conductive link affects a frequency performance of the probe feed.

9. The method according to claim 6, wherein the forming the conductive link comprises depositing conductive material on an end face of the body.

10. The method according to claim 9, wherein the forming of the conductive link comprises at least one of etching, patterning, printing, sputtering, vacuum deposition, ion vapour deposition.

11. The method according to claim 6, wherein the conductive link includes a capacitive coupling.

12. The method according to claim 11, wherein the capacitive coupling at least one of affects a high frequency connection to the waveguide ground plane or prevents a direct current (DC) path to the waveguide ground plane.

13. The method according to claim 1, further comprising filling the void with the conductive material.

14. The method according to claim 1, wherein forming the body comprises forming the body using an injection moulding process.

15. The method according to claim 14, wherein the injection moulding process comprises injection moulding the dielectric material.

16. The method according to claim 1, wherein the conductive material comprises at least one of silver, gold, nickel or an alloy thereof.

17. The method according to claim 1, wherein the medical microwave applicator is formed to be at least one of releasably attachable or releasably detachable to a coupling for applying electromagnetic radiation to a waveguide component of the medical microwave applicator via the probe feed.

18. The method according to claim 17, wherein the method comprises forming a plurality of medical microwave applicators, each having different frequency transmission characteristics, and each at least one of releasably attachable or releasably detachable to the coupling.

19. The method according to claim 17, wherein the void and the conductive material are formed so that, when the coupling is attached to the medical microwave applicator there is at least one continuous electrically conductive path between the coupling and the dielectric material via the conductive material.

20. The method according to claim 19, wherein the at least one continuous electrically conductive path comprises no air gap.

21. The method according to claim 1, wherein the method comprises installing the body inside a holder, and the medical microwave applicator comprises no tuning components for tuning frequency.

22. The method according to claim 1, wherein the probe feed comprises a transverse magnetic TM mode feed.

23. The method according to claim 1, wherein the probe feed is configured to enter one plane and exit another, to link the conductive material to a waveguide ground plane.

24. The method according to claim 1, wherein the medical microwave applicator comprises the waveguide comprising the dielectric material, the medical microwave applicator is attachable to a coupling for applying electromagnetic radiation to the waveguide via the probe feed, and the depositing of the conductive material comprises depositing the conductive material so that it adheres to the dielectric material to form the probe feed for applying the electromagnetic radiation to the waveguide.

25. The method according to claim 1, wherein the depositing of the conductive material comprises depositing the conductive material so that it adheres to the dielectric material over all of a surface within the void.

26. A method of forming a medical microwave applicator for use in treating tissue comprising:
  forming a body comprising dielectric material so that there is a void in the dielectric material;
  performing a deposition process to deposit conductive material in the void and on an outer surface of the body to create a conductive feature that adheres directly to the dielectric material, the deposited directly adhered conductive feature being a probe feed that partially or entirely fills the void and that couples electromagnetic energy via the directly adhered conductive material of the probe feed into a waveguide comprising the dielectric material such that the electromagnetic energy is transmitted through the dielectric material of the waveguide to an end of the medical microwave applicator for placing adjacent to or in contact with the tissue;
  further performing the deposition process so that the directly adhered conductive material of the probe feed is deposited to have a thickness and configuration to provide a directly adhered transmission structure that receives the electromagnetic energy from a coaxial feed and transmits the electromagnetic energy through the directly adhered conductive material of the probe feed and into the dielectric material; and
  forming a conductive link from the conductive material deposited in the void to conductive material on an outer surface, the outer surface of the conductive material being configured for connection to the coaxial feed to receive the electromagnetic energy via the coaxial feed and the conductive link being arranged so as to launch the electromagnetic energy as a transverse electric (TE) mode.

27. A method of forming a medical microwave applicator for use in treating tissue comprising:
  forming a body comprising dielectric material so that there is a void in the dielectric material;
  performing a deposition process to deposit conductive material in the void, wherein the deposition process comprises a kiln co-fired ceramic plating process to create a conductive feature that adheres directly to the dielectric material, the deposited directly adhered conductive feature being a probe feed that partially or entirely fills the void and that couples electromagnetic energy via the directly adhered conductive material of the probe feed into a waveguide comprising the dielectric material such that the electromagnetic energy is transmitted through the dielectric material of the waveguide to an end of the medical microwave applicator for placing adjacent to or in contact with the tissue;
  further performing the deposition process so that the directly adhered conductive material of the probe feed is deposited to have a thickness and configuration to provide a directly adhered transmission structure that receives the electromagnetic energy from a coaxial feed and transmits the electromagnetic energy through the directly adhered conductive material of the probe feed and into the dielectric material; and
  forming a conductive link from the conductive material deposited in the void to conductive material on an outer surface, the outer surface of the conductive material being configured for connection to the coaxial feed to receive the electromagnetic energy via the coaxial feed and the conductive link being arranged so as to launch the electromagnetic energy as a transverse electric (TE) mode.

* * * * *

UNITED STATES PATENT AND TRADEMARK OFFICE
CERTIFICATE OF CORRECTION

Page 1 of 2

PATENT NO. : 10,335,231 B2
APPLICATION NO. : 14/364404
DATED : July 2, 2019
INVENTOR(S) : Gary Beale and Eamon McErlean It is certified that error appears in the above-identified patent and that said Letters Patent is hereby corrected as shown below:

In the Drawings

Figure 13 should be deleted and the attached fig. 13 should be inserted as shown on the attached page.

Signed and Sealed this
Twenty-ninth Day of October, 2019

Andrei Iancu
*Director of the United States Patent and Trademark Office*